(12) United States Patent
Blanvalet et al.

(10) Patent No.: US 9,833,392 B2
(45) Date of Patent: Dec. 5, 2017

(54) TOOTH VARNISH COMPOSITIONS AND METHODS FOR THEIR USE

(71) Applicants: Colgate-Palmolive Company, New York, NY (US); Edward Joziak, Monroe Township, NJ (US)

(72) Inventors: Claude Blanvalet, Angleur (BE); Andre Morgan, Robbinsville, NJ (US); Michael Prencipe, Princeton Junction, NJ (US); Marilou Joziak

(73) Assignee: Colgate-Palmolive Company, New York, NY (US)

(*) Notice: Subject to any disclaimer, the term of this patent is extended or adjusted under 35 U.S.C. 154(b) by 14 days.

(21) Appl. No.: 15/037,798

(22) PCT Filed: Nov. 19, 2013

(86) PCT No.: PCT/US2013/070679
§ 371 (c)(1),
(2) Date: May 19, 2016

(87) PCT Pub. No.: WO2015/076777
PCT Pub. Date: May 28, 2015

(65) Prior Publication Data
US 2016/0303007 A1    Oct. 20, 2016

(51) Int. Cl.
| A61K 8/19 | (2006.01) |
| A61K 8/73 | (2006.01) |
| A61K 8/31 | (2006.01) |
| A61K 8/34 | (2006.01) |
| A61K 6/00 | (2006.01) |
| A61K 8/92 | (2006.01) |
| A61Q 11/00 | (2006.01) |
| A61K 8/18 | (2006.01) |

(52) U.S. Cl.
CPC .............. *A61K 8/19* (2013.01); *A61K 6/0017* (2013.01); *A61K 8/18* (2013.01); *A61K 8/31* (2013.01); *A61K 8/34* (2013.01); *A61K 8/731* (2013.01); *A61K 8/922* (2013.01); *A61K 8/927* (2013.01); *A61Q 11/00* (2013.01); *A61K 2800/30* (2013.01)

(58) Field of Classification Search
CPC .................................. A61K 31/136; A61K 8/19
USPC ......................................................... 424/468
See application file for complete search history.

(56) References Cited

U.S. PATENT DOCUMENTS

| 5,139,768 A | 8/1992 | Friedman |
| 5,395,241 A | 3/1995 | Kandelman |
| 5,403,577 A | 4/1995 | Friedman |
| 5,849,266 A | 12/1998 | Friedman |
| 6,491,898 B1 | 12/2002 | Yamagishi et al. |
| 7,264,882 B2 * | 9/2007 | Engelbrecht ......... A61K 6/0017 428/447 |
| 2004/0102554 A1 | 5/2004 | Patacca et al. |
| 2006/0105028 A1 | 5/2006 | Zhang et al. |
| 2007/0041913 A1 | 2/2007 | Urai et al. |
| 2007/0122360 A1 | 5/2007 | Oniki et al. |
| 2009/0081291 A1 * | 3/2009 | Gin ........................ A61K 8/02 424/468 |
| 2009/0142282 A1 | 6/2009 | Kendall et al. |
| 2009/0191279 A1 | 7/2009 | Kennard et al. |
| 2011/0033394 A1 | 2/2011 | Blanvalet et al. |
| 2012/0156153 A1 | 6/2012 | Fogg et al. |

FOREIGN PATENT DOCUMENTS

| EP | 0381445 | 8/1990 |
| WO | WO 02/011681 | 2/2002 |
| WO | WO 2004/045446 | 6/2004 |
| WO | WO 2009/158564 | 11/2009 |
| WO | WO 2011/062805 | 5/2011 |

OTHER PUBLICATIONS

Dow Chemicals: "Ethocel: Ethylcellulose Polymers Technical Handbook", Published Sep. 2005, pp. 4-25, http://www.dow.com/dowwolf/en/pdf/192-00818.pdf [retrieved 2012 Oct. 2008].
International Search Report and Written Opinion in International Application No. PCT/US2013/070679, dated Jul. 16, 2014.

* cited by examiner

*Primary Examiner* — Walter Webb

(57) ABSTRACT

The disclosure provides hypersensitivity preventative tooth varnish compositions comprising, inter alia, ethyl cellulose and fluoride, and methods for the use of such compositions for the treatment of hypersensitive teeth.

19 Claims, No Drawings

TOOTH VARNISH COMPOSITIONS AND METHODS FOR THEIR USE

BACKGROUND

Fluoride compositions are routinely applied to teeth by any number of methods and compositions, the most common being by utilizing fluoride containing dentifrice compositions, such as toothpastes and mouthwashes.

However, there are certain situations where it is desirable to have prolonged contact of the fluoride compositions with teeth, and to use amounts of fluoride that exceed fluoride amounts present in dentifrice compositions.

For example, it may be desirable to treat xerostomia (dry mouth), tooth hypersensitivity, dental caries with high levels of fluoride for prolonged periods of time.

Thus, tooth varnish compositions have been developed, which are applied directly to tooth surfaces, for example by spray or using a brush. The film that forms upon evaporation of solvent from the tooth surface allows for a longer exposure time (e.g., about or greater than 2 hours) before the composition is worn away by mechanical means such as brushing and chewing food.

One disadvantage of tooth varnishes, and in particular tooth varnishes that contain natural film-forming ingredients such as shellac and shellac wax, is that they may in some cases have a tendency to be less than completely uniform from batch to batch, thus affecting rheological properties such as viscosity which can potentially result in uneven application of fluoride (or other active ingredient) or increased difficulty in applying the composition to tooth surfaces.

Thus, there is a need for improved tooth varnish compositions that contain appropriate synthetic materials for inclusion in tooth varnish that provide good manufacturing, application and performance properties, especially in non-aqueous tooth varnish compositions.

SUMMARY

Unless otherwise indicated, the terms "%" or "percent" when used in connection with an ingredient of the tooth varnish compositions of the invention is intended to refer to the percent by wet weight of the indicated ingredient in the tooth varnish composition.

In some embodiments, the present invention provides a non-aqueous hypersensitivity preventative tooth varnish composition comprising: a fluoride source; ethyl cellulose in an amount effective to achieve suspension of the fluoride source; mastic; and a non-aqueous solvent; wherein i) the fluoride source is present in an amount equal to or greater than the amount of ethyl cellulose; and ii) the tooth varnish composition does not contain either shellac or shellac wax.

In some embodiments, the tooth varnish compositions of the invention further comprise colophonium.

In some embodiments, the tooth varnish compositions of the invention further comprise beeswax.

In some embodiments, the tooth varnish compositions of the invention comprise a fluoride source; ethyl cellulose in an amount effective to achieve suspension of the fluoride source; a plant resin selected from mastic, colophonium and combinations thereof; and a non-aqueous solvent; wherein: i) the fluoride source is present in an amount equal to or greater than the amount of ethyl cellulose; and ii) the tooth varnish composition does not contain either shellac or shellac wax. In one embodiment of this aspect of this embodiment, the varnish further comprises beeswax.

In some embodiments, the ethyl cellulose is present in an amount of up to 5%, preferably from 1% to 5%, or from 1% to 4%, more preferably from 2% to 3%, for example 2.5%, by weight of the composition.

In further embodiments of the tooth varnish compositions of the invention, the fluoride source is sodium fluoride, which is present in an amount of from 4% to 10%, or 5%, or 6%, or 7%, or 8%, or 9%, by weight of the composition. Generally, the amount of the fluoride source is equal to or greater than the amount of ethyl cellulose in the tooth varnish composition.

In some embodiments of the tooth varnish compositions of the invention, colophonium is optionally present in the tooth varnish composition in an amount of from 25% to 40%, or 30% to 35%, or 31%, 32%, 33% or 34%; mastic is present in the tooth varnish composition: 1) when colophonium also is present in an amount of from 25% to 35%, or 27% to 32%, or 28% to 31%, or 29% or 30%, and 2) when colophonium is not present, in an amount of from 50% to 70%, or 55% to 65%, or 58% to 62%, or 60%, 61% or 62%; and beeswax is present in the tooth varnish composition in an amount of from 1% to 5%, or 2%, or 3%, or 4% or 5%, by weight of the composition.

In some embodiments of the tooth varnish compositions of the invention, the beeswax is white beeswax.

In some embodiments of the tooth varnish compositions of the invention, the ethyl cellulose is N100PH.

In some embodiments of the tooth varnish compositions of the invention, the non-aqueous solvent is 96% ethanol, which is present in an amount of from 20% to 40%, or from 25% to 35%, or from 25% to 30%, or 25%, 26%, 27%, 28%, 29% or 30%, by weight of the composition.

In some embodiments, the tooth varnish compositions of the invention comprise: sodium fluoride in an amount of from 4% to 6%; ethyl cellulose, preferably N100PH, in an amount of from 1% to 5%; or from 2% to 3%; colophonium in an amount of from 30% to 35%; mastic in an amount of from 28% to 30%; beeswax, preferably white beeswax, in an amount of from 2% to 4%; and 96% ethanol solvent in an amount of from 25% to 30%, by weight of the composition.

In some embodiments, the tooth varnish compositions of the invention further comprise one or more sweetening agents, and/or one or more flavoring agents.

The present invention also provides methods of preventing dental hypersensitivity, and methods for treating a symptom of dental hypersensitivity, in a human or a domesticated animal, comprising application of a tooth varnish composition of the invention to the teeth or gingival tissues of an animal. In some embodiments, the application is by brush, or by spray.

DETAILED DESCRIPTION

It has been discovered in accordance with the present invention that ethyl cellulose can be employed at relatively low concentration in a tooth varnish composition containing a colophonium/mastic based film forming component to effectively suspend a fluoride-containing active (e.g., sodium fluoride) in the composition. The use of the synthetic ethyl cellulose in place of naturally occurring tooth varnish suspending components (such as shellac and shellac wax), possesses significant advantages in terms of increased consistency of the varnish composition.

Accordingly, in one embodiment, the present invention provides a non-aqueous hypersensitivity preventative tooth varnish composition comprising: a fluoride source; ethyl cellulose in an amount effective to achieve suspension of the fluoride source; mastic; beeswax; and a non-aqueous solvent; wherein i) the fluoride source is present in an amount equal to or greater than the amount of ethyl cellulose; and ii) the tooth varnish composition does not contain either shellac or shellac wax.

The ethyl cellulose is employed in the compositions of the invention in an amount effective to achieve suspension of the fluoride source. That is, an amount effective to provide an even suspension of fluoride containing particles, without significant phase separation and/or precipitation.

Ethyl cellulose is an ether derivative of cellulose. Cellulose is a natural polysaccharide made up of long chains of β anhydroglucose units joined together by acetal linkages. Each anhydroglucose unit has three hydroxyl groups, which may form ethyl ethers, e.g., by the reaction of ethyl chloride with alkali cellulose, thus providing ethyl cellulose. The degree of ethoxylation varies in different ethyl cellulose products. Complete substitution of all three groups on the anhydroglucose units would give the triethyl ether possessing a substitution value of 3, or 54.88% ethoxyl. The completely substituted triethylcellulose, however, lacks strength and flexibility, is not thermoplastic, and shows extremely limited compatibility and solubility. The degree of substitution, as well as the molecular weight, affects the viscosity and solubility of the product. In certain embodiments, the ethyl cellulose has an average substitution value of between 2.25 and 2.60 ethoxyl groups per anhydroglucose unit, or 44-52% ethoxyl content. In a particular embodiment, the ethyl cellulose has an average substitution value of 2.46-2.58 ethoxyl groups per anhydroglucose unit, corresponding to an ethoxyl content of 48-49.5%.

Preferably, the ethyl cellulose has a viscosity of 50-200 cps, preferably from 80-120 cps, more preferably from 90-110 cps or 80-105 cps, for example about 100 cps, e.g., wherein viscosity is measured using 5% ethyl cellulose in 80 parts toluene: 20 parts ethanol at 25° C.

Examples of preferred ethyl celluloses useful in the present invention include Aqualon® N100 ethyl cellulose (Hercules Corp.) and Ethocel® Standard 100 (Dow Chem. Co.). One particularly preferred ethyl cellulose is N100PH.

The ethyl cellulose is employed in the compositions of the invention at relatively low concentrations, for example up to 5%, preferably from 1% to 5%, or from 1% to 4%, more preferably from 2% to 3%, for example 2.5%, by weight of the composition. In contrast to many other ethyl cellulose-containing compositions, the ethyl cellulose concentration in the compositions of the invention is less than or equal to the concentration of the fluoride-containing active (e.g., sodium fluoride).

The formulations also contain natural resins and waxes. For example, the formulations comprise (i) mastic, a resin obtained from the mastic tree (*Pistacia lentiscus*); (ii) beeswax, e.g., white beeswax, a natural wax produced by honey bees Opts spp.) primarily comprising esters of fatty acids and various long chain alcohols.; and (in some embodiments) (iii) colophonium, a translucent yellowish to brownish resin derived from the stumps or sap of various plants, e.g. certain pine and conifer species.

While not wishing to be bound by any theory, it is believed that at the concentrations employed, the ethyl cellulose in the compositions of the invention functions, inter alia, as a suspending agent fir the fluoride-containing active ingredient. It is surprising that ethyl cellulose at these relatively low concentrations imparts the requisite increased viscosity properties sufficient to allow its use as a suspension agent in the compositions of the invention.

The tooth varnish compositions of the present invention contain a fluoride source—i.e., a fluoride-containing compound having a beneficial effect on the care and hygiene of the oral cavity, e.g. diminution of enamel solubility in acid and protection of the teeth against decay. Typical sources of fluoride include soluble salts of the fluoride ion; such as, for example: sodium fluoride, potassium fluoride, calcium fluoride, zinc fluoride, zinc ammonium fluoride, lithium fluoride, ammonium fluoride, stannous fluoride, stannous fluorozirconate, and complex fluorides, monofluorophosphates and salts thereof such as, e.g., sodium monofluorophosphate or potassium monofluorophosphate, laurylamine hydrofluoride, diethylaminoethyloctoylamide hydrofluoride, didecyldimethylammonium fluoride, cetylpyridinium fluoride, dilaurylmorpholinium fluoride, sarcosine stannous fluoride, glycine potassium fluoride, glycine hydrofluoride, and amine fluorides. The fluoride ion source may be presented as a salt or a slime preparation. Preferably, the fluoride ion source is in the form of a salt. One particularly preferred fluoride ion source is sodium fluoride.

The fluoride ion source is most preferably present in an amount such that it is capable of providing a high level of fluoride ion in the composition, that is at least about 5,000 ppm, and in some instances up to as much as 50,000 ppm, e.g., from about 7,000 ppm to about 40,000 ppm, from about 15,000 ppm to about 30,000 ppm, or about 22,000 or 23,000 ppm. In order to provide such a concentration in the optimal ppm range, the exact weight percentage of the fluoride ion source in the composition may vary, depending upon the stoichiometric properties of different fluoride ion sources. Nevertheless, in preferred embodiments, the fluoride ion source is sodium fluoride, which is present in the composition is an amount of from 4% to 10%, or 5%, or 6%, or 7%, or 8%, or 9%, by weight of the composition. Generally, the fluoride source is present in an amount equal to or greater than the amount of ethyl cellulose.

The compositions of the invention are intended to be applied, for example by a brush or spray, to a dental surface, that is, a surface within the oral cavity such as the buccal and lingual surfaces of teeth, and to form a film upon evaporation of solvent. The resulting film, which is formed in situ, allows the suspended active fluoride source to remain in contact with the tooth surfaces for a period of time, typically until the film is removed by physical means, e.g., brushing or chewing food. Thus, the compositions of the invention contain a film-forming component, which includes mastic and beeswax, preferably white beeswax, and optionally colophonium (also known as rosin). Preferably, the mastic is present in the tooth varnish composition: 1) when colophonium also is present in an amount of from 25% to 35%, or 27% to 32%, or 28% to 31%, or 29% or 30%, and 2) when colophonium is not present, in an amount of from 50% to 70%, or 55% to 65%, or 58% to 62%, or 60%, 61% or 62%; and the beeswax is present in the tooth varnish composition in an amount of from 1% to 5%, or 7%, or 3%, or 4% or 5%, by weight of the composition. Mastic and colophonium are both well known in the art, and widely available.

The compositions of the invention contain one or more non-aqueous solvents. Preferably, the solvent (or combination of solvents) is non-toxic, and rapidly evaporates when the compositions of the present invention are applied to the teeth. Suitable solvents include methanol, ethanol, ethyl acetate, acetone, and isopropanol. As noted above, the compositions of the invention are non-aqueous—i.e. they contain no added water. Preferably, the compositions of the invention are substantially free of water, e.g., contain 0% water, or less than 1%) water by weight. Nevertheless, as used herein, the term non-aqueous is intended to include such trace amounts of water as may be present in certain components of the compositions of the invention, for example through their manufacturing processes, and also specifically includes the water present in 96% ethanol, which is a preferred solvent for the compositions of the invention, and which is preferably present in an amount of from 20% to 40%, or from 2% to 35%, or from 25% to 30%, or 25%, 26%, 27%, 78%, 29% or 30%, by weight of the composition.

The compositions of the invention preferably have viscosities of greater than 3000 centipoise (cps), preferably between 4000 cps and 14,000 cps, for example about 5000, 6000, 7000, 8000, 9000, 10,000, 11,000, 12,000, 13,000 or 14,000 cps.

In addition, the compositions also are thixotropic, and thus more easily spread during application. Such relatively high viscosity and thixotropic characteristics reduce and/or prevent the tendency of the composition to run or drip upon application to tooth surfaces.

In some embodiments described above, the tooth varnish compositions of the invention can further include one or more sweetening agents, flavoring agents and coloring agents. Any suitable flavoring or sweetening material may be employed. Examples of suitable flavoring constituents include flavoring oils, e.g. oil of spearmint, peppermint, wintergreen, clove, sage, eucalyptus, marjoram, cinnamon, lemon, raspberry and orange, and methyl salicylate. Suitable sweetening agents include sucrose, lactose, maltose, xylitol, sodium cyclamate, perillartine, AMP (aspartyl phenyl alanine methyl ester), saccharin and the like. Suitably, flavor and sweetening agents may each or together comprise from up to 5%, or up to 4%, or up to 3%, or up to 2%, or up to 1%, or from 0.5% to 1%, by weight of the composition.

As will be evident to one of skill in the art, some components of the invention may perform multiple functions, and the identification of a compound as having one function herein is not meant to exclude its use for other functions in a particular composition.

It is also understood that compounds in formulation may naturally react, disassociate, and/or form complexes with one another. Accordingly, certain ingredients may be formed in situ, and also may in formulation exist in different forms (for example, to the extent the sodium fluoride is dissolved, it will naturally disassociate into separate sodium and fluoride ions, as opposed to a solid salt). As is usual in the art, the compositions of the invention are described in terms of exemplary formulation ingredients, without intending to exclude combinations of other ingredients that result in the same final compositions, or to exclude the natural reaction products of the described ingredient combinations.

Various other materials may be incorporated in the oral preparations of this invention such as whitening agents, including urea peroxide, calcium peroxide, titanium dioxide, hydrogen peroxide, complexes of polyvinylpyrolidone (PVP) and hydrogen peroxide, preservatives, vitamins such as vitamin B6, B12, E and K, silicones, chlorophyll compounds, potassium salts for the treatment of dental hypersensitivity such as potassium nitrate as well as antitartar agents such as sodium tripotyphosphate and di- and tetra-alkali metal pyrophosphate salts such as di- and tetrasodium pyrophosphate, as well as calcium based salts such as dicalcium phosphate, tricalcium phosphate, precipitated calcium carbonate either alone or in combination with amino acids such as L-arginine. These agents, when present, are incorporated in the compositions of the present invention in amounts which do not substantially adversely affect the properties and characteristics desired.

In general, each of the foregoing adjuvants may be typically incorporated in the instant tooth varnishes in amounts up to 5% provided they do not adversely affect the desirable properties of the compositions of the present invention.

The present invention also provides methods of preventing dental hypersensitivity, and methods for treating a symptom of dental hypersensitivity, in a human or a domesticated animal, comprising application of a tooth varnish composition of the invention to the teeth or gingival tissues of a human or a domesticated animal. In some embodiments, the application is by brush, or by spray.

As used herein, the term "domesticated animal" includes animals generally recognized to be pets, for example dogs and cats.

The invention thus provides, in one embodiment, a hypersensitivity preventative tooth varnish composition comprising: a fluoride source; ethyl cellulose in an amount effective to achieve suspension of the fluoride source; a plant resin selected from mastic, colophonium and combinations thereof; beeswax; and a non-aqueous solvent; wherein i) the fluoride source is present in an amount equal to or greater than the amount of ethyl cellulose; and ii) the tooth varnish composition does not contain either shellac or shellac wax (Composition 1), for example:

1.1. Composition 1, wherein the plant resin comprises a combination of mastic and colophonium.

1.2. Any foregoing composition wherein the ethyl cellulose is present in an amount of up to 5%, preferably from 1% to 5%, or from 1% to 4%, more preferably from 2% to 3%, for example 2.5%, by weight of the composition.

1.3. Any foregoing composition wherein the fluoride source is sodium fluoride, which is present in an amount of from 4% to 10%, or 5%, or 6%, or 7%, or 8%, or 9%, by weight of the composition.

1.4 Any foregoing composition wherein the plant resin is present in an amount of 50% to 75%, e.g., 60-70%, of the composition by weight.

1.5. Any foregoing composition wherein the beeswax is present in the amount of 1% to 5% by weight.

1.6. Any foregoing composition wherein (a) colophonium colophonium is optionally present in the tooth varnish composition in an amount of from 25% to 40%, or 30% to 35%, or 31%, 32%, 33% or 34%, by weight of the composition; (b) mastic is present in the tooth varnish composition: 1) when colophonium also is present in an amount of from 25% to 35%, or 27% to 32%, or 28% to 31%, or 29% or 30%, and 2) when colophonium is not present, in an amount of from 50% to 70%, or 55% to 65%, or 58% to 62%, or 60%, 61% or 62%, by weight of the composition; and (c) the beeswax is present in the tooth varnish composition in an amount of from 1% to 5%, or 2%, or 3%, or 4% or 5%, by weight of the composition; and beeswax is present in the tooth varnish composition in an amount of from 1% to 5%, or 2%, or 3%, or 4% or 5%, by weight of the composition.

1.7. Any foregoing composition wherein the beeswax is white beeswax.

1.8. Any foregoing composition wherein the ethyl cellulose has an average substitution value of between 2.25 and 2.60 ethoxyl groups per anhydroglucose unit, e.g., 44-52% ethoxyl content.-

1.9 Any foregoing composition wherein the ethyl cellulose has an average substitution value of 2.46-2.58 ethoxyl groups per anhydroglucose unit, e.g. an ethoxyl content of 48-49.5%.

1.10. Any foregoing composition wherein the ethyl cellulose has a viscosity of 50-200 cps, e.g. from 80-120 cps, for example 90-110 cps or 80-105 cps, for example about 100 cps, e.g., wherein viscosity is measured at about 25° C. using a 5% solution of ethyl cellulose in a solvent made up of 80 parts toluene: 20 parts ethanol.

1.11. Any foregoing composition wherein the ethyl cellulose is Aqualon® N100 ethyl cellulose; Ethocel® Standard 100; or N100PH.

1.12. Any foregoing composition wherein the non-aqueous solvent is 96% ethanol, which is present in an amount of from 20% to 40%, or from 25% to 35%, or from 25% to 30%, or 75%, 26%, 27%, 28%, 29% or 30%, by weight of the composition.

1.13. Any foregoing composition comprising: sodium fluoride in an amount of from 4% to 6%, by weight of the composition; ethyl cellulose, in an amount of from 2% to 3%, by weight of the composition; colophonium in an amount of from 30% to 35%, by weight of the composition; mastic in an amount of from 28% to 30%, by weight of the composition; beeswax, preferably white beeswax, in an amount of from 2% to 4%, by weight of the composition; and 96% ethanol solvent in an amount of from 25% to 30%, by weight of the composition.

1.14. Any foregoing composition comprising: sodium fluoride in an amount of 5% by weight of the composition; ethyl cellulose in an amount of 2.5%, by weight of the composition; colophonium in an amount of from 32% to by weight of the composition; mastic in an amount of from 29% to 30%, by weight of the composition; beeswax, preferably white beeswax, in an amount of 3%, by weight of the composition; and 96% ethanol solvent in an amount of from 27% to 28%, by weight of the composition.

1.15. Any foregoing composition comprising one or more sweeteners and/or flavoring agents.

1.16. Any of the foregoing compositions wherein the composition is substantially non-aqueous, e.g., comprising less than 5% water, e.g., less than 4%, 3%, 2% or 1% water.

The invention further provides, in another embodiment, the use of ethyl cellulose in the manufacture of a tooth varnish according to any of Compositions 1, et seq.

The following examples are further illustrative of the nature of the present invention, but it is understood that the invention is not limited thereto. All amounts and proportions referred to herein and in the appended claims are by weight, unless otherwise indicated.

EXAMPLES

Example 1—Evaluation of Ethyl Cellulose, PVP and Increased Mastic/Colophonium Compared to Shellac/Shellac Wax in Tooth Varnish Ethyl cellulose, PVP, and increasing amounts of colophonium and mastic are evaluated as replacements for shellac and shellac wax in a commercial non-aqueous tooth varnish. Table 1 shows the compositions of the commercial formula, experimental formulas 1-4, and a composition according to the invention (formula 5).

TABLE 1

Compositions of Tooth Varnish Formulas

| Ingredient | Commercial Formula | 1 | 2 | 3 | 4 | 5 |
|---|---|---|---|---|---|---|
| 96% ethanol | 27.16 | 27.16 | 27.16 | 27.16 | 27.16 | 27.16 |
| Colophonium | 32.33 | 51.56 | 32.33 | 32.33 | 41.95 | 32.33 |
| Sodium Fluoride | 5 | 5 | 5 | 5 | 5 | 5 |
| Mastic | 11.95 | 11.95 | 31.18 | 28.68 | 21.57 | 29.18 |
| White Beeswax | 0.49 | 3 | 3 | 3 | 3 | 3 |
| Saccharin | 0.69 | 0.69 | 0.69 | 0.69 | 0.69 | 0.69 |
| Shellac Wax | 1.3 | — | — | — | — | — |
| Shellac type 101 | 20.44 | — | — | — | — | — |
| Ethyl Cellulose (N100PH) | — | — | — | — | — | 2.5 |
| PVP (Polyclar 10) | — | — | — | 2.5 | — | — |
| Flavor | 0.64 | 0.64 | 0.64 | 0.64 | 0.64 | 0.64 |
| Viscosity (cps) | 4264 | 1069 | 1231 | 1481 | 1171 | 11168 |
| Cosmetic Assessment | Good | Poor | Poor | Poor | Poor | Good |

Shellac and shellac wax replacement formulations are initially made by increasing the level of beeswax, colophonium, and/or mastic. As shown in Table 1, the resulting compositions 1-4 possess lower viscosities and do not provide a proper consistency of the composition, either for stability in formulation or for even application and cosmetic appearance on application. The compositions 1-4 also display an unacceptable phase separation, permitting settling of the active ingredient, which would cause uneven delivery of the fluoride from application to application.

The increase in beeswax, colophonium, and/or mastic do not give the viscosity needed to suspend the sodium fluoride, and also result in compositions with unacceptable phase separation. The further addition of a conventional viscosity modifying agent, polyvinyl pyrrolidone (formula 3) also does not solve the problem.

In contrast, the addition of ethyl cellulose as a shellac and shellac wax replacement (formula 5) shows an unanticipated benefit to the composition viscosity. The resulting composition possesses an increased viscosity suitable to suspend the sodium fluoride in the formula, and does not result in an unacceptable phase separation. While ethyl cellulose is well known for its film forming properties, its ability to build viscosity, in particular at the relatively low level used in the compositions of the present invention, is both unexpected and surprising.

Example 2—Evaluation of Hydroxypropyl Cellulose Compared to Shellac/Shellac Wax in Tooth Varnish The use of hydroxypropyl cellulose (HPC), is also evaluated as a replacement for shellac and shellac wax. Other celluloses (e.g. carboxymethyl cellulose and hydroxymethyl cellulose) are not considered suitable, as they are not soluble in ethanol-only based systems, and require some water to dissolve.

Table 2 shows the results of experiments using HPC in the formulations, which included HPC (i.e., "Kucel Gum"; the trade name for the HPC used), in placed of shellac, shellac wax and colophonium.

TABLE 2

Evaluation of Hydroxypropyl Cellulose in Tooth Varnish Formulas

| Ingredient | 6 | 7 | 8 | 9 | 10 |
|---|---|---|---|---|---|
| 96% ethanol | 27.16 | 27.16 | 27.16 | 27.16 | 27.16 |
| Thickening Silica | 2 | 2 | 2 | — | 1 |
| Sodium Fluoride | 5 | 5 | 5 | 5 | 5 |
| Mastic | 60.51 | 60.01 | 59.51 | 61.51 | 60.01 |
| White Beeswax | 3 | 3 | 3 | 3 | 3 |
| Saccharin | 0.69 | 0.69 | 0.69 | 0.69 | 0.69 |
| Shellac Wax | — | — | — | — | — |
| Shellac type 101 | — | — | — | — | — |
| Kucel Gum (HPC) | 1 | 1.5 | 2 | 2 | 2.5 |
| Ethyl Cellulose (N100PH) | — | — | — | — | — |
| Flavor | 0.64 | 0.64 | 0.64 | 0.64 | 0.64 |
| Viscosity (cps) | 2556 | 3165 | Could not determine (lumps) | 3447 (lumps) | Too viscous/ white lumps |

At concentrations of up to 1.5% the resulting compositions does not possess sufficient viscosity to suitably suspend sodium fluoride, and at 2-2.5%, white lumps are observed to form in the batch, again making the formula unacceptable. Thus, the beneficial properties of ethyl cellulose described above are not possessed by hydroxypropyl cellulose.

Example 3—Evaluation of Tooth Varnish Formulation Containing Ethyl Cellulose without Colophonium The use of ethyl cellulose hydroxypropyl is also evaluated in tooth varnish compositions with increased concentration of mastic in place of colophonium. The results are shown in Table 3 below.

TABLE 3

Compositions of Tooth Varnish Formulas Without Colophonium

| Ingredient | 11 | 12 | 13 |
|---|---|---|---|
| 96% ethanol | 27.16 | 27.16 | 27.16 |
| Colophonium | — | — | — |
| Thickening Silica | 1 | — | — |
| Sodium Fluoride | 5 | 5 | 5 |
| Mastic | 60.01 | 62.01 | 61.01 |
| White Beeswax | 3 | 3 | 3 |
| Saccharin | 0.69 | 0.69 | 0.69 |
| Shellac Wax | — | — | — |
| Shellac type 101 | — | — | — |
| Ethyl Cellulose (N100PH) | 2.5 | 1.5 | 2.5 |
| Flavor | 0.64 | 0.64 | 0.64 |
| Viscosity (cps) | 12502 | 5716 | 8546 |

Compositions with increased mastic and ethyl cellulose in place of shellac and shellac wax, but without colophonium, possesses suitable viscosities, both with (formula 11) and without (formulae 12 and 13) additional thickening silica, although the cosmetic properties were not as good as Formula 5.

While the present invention has been described with reference to embodiments, it will be understood by those skilled in the art that various modifications and variations may be made therein without departing from the scope of the present invention as defined by the appended claims.

We claim:

1. A hypersensitivity preventative tooth varnish composition comprising:
    a fluoride source;
    ethyl cellulose in an amount effective to achieve suspension of the fluoride source;
    a plant resin selected from mastic, colophonium and combinations thereof; and
    a non-aqueous solvent;
    wherein:
        i) the fluoride source is present in an amount equal to or greater than the amount of ethyl cellulose; and
        i) the tooth varnish composition does not contain either shellac or shellac wax.

2. The tooth varnish composition of claim 1, wherein the plant sin comprises a combination of mastic and colophonium.

3. The tooth varnish composition of claim 1, wherein the ethyl cellulose is present in an amount of 1% to 5%, by weight of the composition.

4. The tooth varnish composition of claim 1, wherein the fluoride source is sodium fluoride, which is present in an amount of from 4% to 10%, by weight of the composition.

5. The tooth varnish composition of claim 1, wherein the composition further comprises beeswax.

6. The tooth varnish composition of claim 5, wherein
    the plant resin is present in an amount of 50% to 75% by weight; and
    the beeswax is present in an amount of from 1% to 5%, by weight.

7. The tooth varnish composition of claim 5, comprising:
    sodium fluoride in an amount of from 4% to 6%;
    ethyl cellulose in an amount of from 2% to 3%;
    colophonium in an amount of from 30% to 35%;
    mastic in an amount of from 28% to 30%;
    beeswax in an amount of from 2% to 4%; and
    wherein the non-aqueous solvent comprises 96% ethanol in an amount of from 25% to 40%, by weight of the composition.

8. The tooth varnish composition of claim 5, wherein the beeswax is white beeswax.

9. The tooth varnish composition of claim 1, wherein the ethyl cellulose has an average substitution value of between 2.25 and 2.60 ethoxyl groups per anhydroglucose unit.

10. The tooth varnish composition of claim 1, wherein the ethyl cellulose has a viscosity of 50-200 cps, wherein viscosity is measured at about 25° C. using 5% solution of ethyl cellulose in a solvent made up of 80 parts toluene: 20 parts ethanol.

11. The tooth varnish composition of claim 7, wherein the 96% ethanol comprises an amount of from 20% to 30% by weight of the composition.

12. The tooth varnish composition of claim 1, wherein the non-aqueous solvent is 96% ethanol.

13. The tooth varnish composition of claim 1, further comprising one or more sweetening agents, for example saccharin; flavoring agents for example raspberry flavoring; or both sweetening agents and flavoring agents, each of which can be present in the tooth varnish composition in an amount of up to 5%, or up to 4%, or up to 3%, or up to 2%, or up to 1%, or from 0.5% to 1%, by weight of the composition.

14. The tooth varnish composition of claim 1, comprising less than 5% water.

15. A method of preventing dental hypersensitivity or treating a symptom of dental hypersensitivity comprising application of the varnish composition of claim 1 to the teeth or gingival tissues of an animal.

16. The method of claim 15, wherein said application is by brush.

17. The method of claim 15, wherein said application is by spray.

18. The method of claim 15, wherein said animal is a human.

19. The method of claim 15, wherein said animal is a domesticated animal.

* * * * *